United States Patent [19]

Meadows

[11] Patent Number: 5,518,731
[45] Date of Patent: * May 21, 1996

[54] NONAQUEOUS FLUORINATED DRUG DELIVERY VEHICLE SUSPENSIONS

[75] Inventor: David L. Meadows, Mission Viejo, Calif.

[73] Assignee: Allergan, Inc., Irvine, Calif.

[ * ] Notice: The portion of the term of this patent subsequent to Dec. 22, 2009, has been disclaimed.

[21] Appl. No.: 260,482

[22] Filed: Jun. 14, 1994

Related U.S. Application Data

[63] Continuation of Ser. No. 853,827, Mar. 19, 1992, abandoned, which is a continuation-in-part of Ser. No. 588,697, Sep. 27, 1990, Pat. No. 5,173,298.

[51] Int. Cl.⁶ .......................... A61K 9/14; A61K 47/34; A61K 47/06; A61K 47/32
[52] U.S. Cl. .................. 424/427; 424/426; 424/428; 424/423; 424/434; 424/435; 424/449; 424/501; 514/912; 514/963
[58] Field of Search .................. 424/427, 423, 424/426, 428, 434, 435, 499, 501, 78.03, 78.04, 78.33; 514/912, 963, 965; 523/122

[56] References Cited

U.S. PATENT DOCUMENTS

| | | | |
|---|---|---|---|
| 3,911,138 | 10/1975 | Clark, Jr. | 424/352 |
| 3,962,439 | 6/1976 | Yokoyama et al. | 424/248 |
| 3,968,245 | 7/1976 | Higuchi | 424/330 |
| 3,989,843 | 11/1976 | Chabert et al. | 424/325 |
| 4,035,506 | 7/1977 | Lucas et al. | 424/303 |
| 4,105,798 | 8/1978 | Moore et al. | 424/352 |
| 4,115,544 | 9/1978 | Shell | 424/14 |
| 4,168,308 | 9/1979 | Wretlind et al. | 424/244 |
| 4,366,169 | 12/1982 | White | 424/285 |
| 4,426,374 | 1/1984 | Wheeler | 424/60 |
| 4,452,818 | 6/1984 | Haidt | 424/352 |
| 4,490,351 | 12/1984 | Clark, Jr. | 424/5 |
| 4,649,047 | 3/1987 | Kaswan | 424/78 |
| 4,826,871 | 5/1989 | Gressel et al. | 514/915 |
| 4,865,846 | 9/1989 | Kaufman | 424/428 |
| 4,882,150 | 11/1989 | Kaufman | 424/428 |
| 4,889,525 | 12/1989 | Yuhas et al. | 600/1 |
| 4,917,930 | 4/1990 | McCormick | 514/832 |
| 4,942,179 | 7/1990 | Borgarello et al. | 514/659 |
| 4,990,283 | 2/1991 | Visca et al. | 514/833 |

FOREIGN PATENT DOCUMENTS

| | | | |
|---|---|---|---|
| 0091313 | 4/1982 | European Pat. Off. | 31/2 |
| 0089815 | 3/1983 | European Pat. Off. | 31/25 |
| 0288659 | 1/1988 | European Pat. Off. | 9/6 |
| 0322249 | 6/1989 | European Pat. Off. | A61K 37/12 |
| 57-21312 | 2/1982 | Japan | A61K 9/06 |
| WO81/00002 | 1/1981 | WIPO | A61K 31/02 |
| 8400686 | 3/1984 | WIPO | A61K 31/66 |
| 9118613 | 12/1991 | WIPO | A61K 31/74 |

OTHER PUBLICATIONS

*International Search Report*, Jul. 2, 1993.

*Primary Examiner*—Edward J. Webman

[57] ABSTRACT

Nonaqueous pharmaceutical compositions for use in aqueous physiological systems are disclosed comprising drug delivery vehicles suspended in nonaqueous perfluorocarbon or fluorinated silicone liquid carriers. The suspended drug delivery vehicles may be water labile or water stable and incorporate therapeutic or diagnostic compounds which remain stable and pharmaceutically effective for extended periods. The pharmaceutical compositions have improved bioavailability, are capable of low dose volume delivery, and do not leach the incorporated therapeutic or diagnostic compounds into the liquid carriers making them well suited for multi-dose packaging and administration.

24 Claims, 2 Drawing Sheets

NONAQUEOUS FLUORINATED DRUG DELIVERY VEHICLE SUSPENSIONS

REFERENCE OF EARLIER APPLICATION

This application is a continuation of application Ser. No. 07/853,827 filed on Mar. 19, 1992, now abandoned, which is a continuation-in-part of application Ser. No. 07/588,697 filed Sep. 27, 1990 and now U.S. Pat. No. 5,173,298, issued Dec. 22, 1992.

FIELD OF THE INVENTION

The present invention relates in general to nonaqueous pharmaceutical compositions intended for use in aqueous physiological systems. More particularly, the present invention is directed to pharmaceutical compositions formed of drug containing microparticulate or microcapsule delivery vehicles suspended in perfluorocarbons or fluorinated silicone liquids. The pharmaceutical compositions of the present invention possess unexpectedly superior shelf-lives, increased bioavailability, prolonged drug delivery profiles and may be configured for convenient multi-dose administration through common routes of pharmaceutical administration including advantageously small volume drop instillation administration.

BACKGROUND OF THE INVENTION

Pharmaceutical medicaments and diagnostic compounds are frequently incorporated into a delivery vehicle for administration to a targeted tissue site. Typically, drug delivery vehicles are formed as aqueous carriers, gels, polymeric material inserts or particulates incorporating a pharmaceutical compound. Once the drug delivery vehicle is placed at the desired delivery site, the pharmaceutical compound is released from the delivery vehicle over a prolonged length of time. The resulting time release profile of the drug is dependent upon a number of variables. Included in these variables are the release mechanism of the drug from the drug delivery vehicle (typically either erosion or diffusion), the amount of drug incorporated into the drug delivery vehicle, the solubility of the drug in the surrounding physiological milieu, and, in the case of particulate delivery vehicles, the particle size or size distribution of the vehicle.

Depending upon the physical characteristics of the vehicle itself as well as those at the intended target site, drug delivery vehicles may be delivered to the target site through a variety of known routes of administration. For example, aqueous based drug delivery solutions may be ingested, injected, inhaled, or applied directly to the skin or mucus membranes as drops, mists, or the like. Conversely, gels and ointments are better suited to direct topical application due to their relatively high viscosities. Similarly, solid polymeric inserts must be physically inserted or affixed to the target site.

A particularly unique target site for pharmaceutical compounds is the ocular environment surrounding the surface of the eye. Aqueous solutions, gels and solid inserts have all been utilized to deliver ocular drugs as the controlled delivery rate characteristics of such known delivery vehicles make them well suited for delivering therapeutic and diagnostic compounds to the ocular environment. However, tear turnover and drainage through the lacrimal system quickly remove a major portion of any compound administered as a drop to the eye so that only a small fraction of the original dosage remains in the eye long enough to be of therapeutic impact. Moreover, unnecessarily high liquid dose volumes inherent in water and oil based delivery systems, result in inefficient use of the delivered drug. Thus, repeated administrations of a drug formulated as an aqueous drop may be required to maintain an effective therapeutic level of the drug in the eye. Thus, pharmaceutical compositions such as ointments, gels or inserts which remain in the eye and gradually release their diagnostic or therapeutic drugs into the ocular environment reduce the need for repeated administrations of the drug to the eye.

Recently, drug delivery vehicles formed of drug-containing erodible microparticles or microcapsules have been developed with some limited success. Such erodible microparticles or microcapsules are designed to be suspended in a liquid carrier medium and delivered to the target tissue through injection, ingestion or using liquid drops. Once at the target site the microparticulates or microcapsules are intended to remain at chat location after the liquid carrier has diffused or drained away. Typically, microparticulates are formed of a drug containing polymer matrix formed in particles ranging from tens to hundreds of microns in diameter. The polymer matrix may be erodible to release the incorporated drug at the target site as the matrix gradually breaks down. Alternatively, the microparticulates may be formed of non-erodible polymers from which the incorporated drug simply diffuses out of and into the target tissue. Microcapsules are comparably sized particles formed of a polymer shell encapsulating the desired pharmaceutical compound. The shell of microcapsules may also be composed of either erodible or non-erodible polymers.

The long term storage of microparticles and microcapsules requires a liquid carrier medium which is physically and chemically compatible with both the polymer of the drug delivery vehicle and the incorporated therapeutic or diagnostic compound as well as the intended physiologic environment. Generally, the liquid carrier of choice is a sterile water solution of the appropriate pH and osmolality. However, a problem with suspending microparticles or microcapsules in aqueous carriers targeted for an aqueous physiological environment is that invariably the incorporated pharmaceutical compound will leach into the aqueous carrier prior to administration. This results in a significant loss of pharmaceutical activity at the site of action as the leached drug contained in the aqueous carrier will be flushed from the target site relatively rapidly.

The tendency of pharmaceutical compounds to leach into the carrier also limits the effective shelf-life of drug delivery vehicles suspended in aqueous carriers. Depending upon the diffusion rate of the incorporated pharmaceutical compound, the shelf-life will normally be much shorter than the preferred shelf-life. Similarly, diffusion of the drug into the aqueous carrier makes it difficult, if not impossible, to formulate pharmaceutical compounds into multiple dose packaging because uniform dose regimens cannot be ensured.

More specifically, pharmaceutical compositions containing drug delivery vehicles utilizing a polymer or drug which is unstable or labile in an aqueous environment cannot be stored for extended lengths of time in their aqueous carriers without significant chemical changes occurring. A significant number of the polymers which are currently being utilized as microparticulate drug delivery vehicles are hydrolytically labile. This characteristic is central to the ability of the polymer matrix to slowly disintegrate and release the drug incorporated in the polymer matrix into the aqueous physiological environment. Since the polymer systems exhibiting hydrolytic instability cannot be stored in aqueous vehicles, they must be stored in a dry state and suspended in the aqueous carrier immediately prior to their administration to the target site. This is a time consuming and burdensome inconvenience to the end user. Moreover, it requires specialized packaging designs which provide a method for separately storing the labile polymer particles and the carrier liquid in appropriate quantities. As a result, the package configuration must be limited to unit dose sizes with the attendant inconvenience and added costs.

Several nonaqueous liquid carriers have been utilized in the art in an attempt to address these problems. Among these are mineral oils, vegetable oils, silicone oils, and free fatty acids. Though generally effective for oral and dermal administration, when used in the ocular environment a significant disadvantage associated with these oils is that they combine with the lipid layer of the tear film which results in a disruption of the film. This in turn may cause the user to experience significant vision blurring and an unacceptable oily sensation. Even if the tear film is not disrupted, the significant difference in the refractive index of the tear film and the refractive index of the oil carrier causes blurring during the residence time of the oil.

A related drawback associated with the ophthalmic drop instillation delivery of pharmaceuticals incorporated in water or oil carrier systems is that conventional small volume droppers have relatively limited delivery volumes restricted to drop sizes that may interfere with vision or be uncomfortable to the user. This is because the density and surface tension characteristics of the typical water and oil based systems do not allow for the practical delivery of less than 35 µl volumes. Thus, because the eye tear film can accommodate only about a 7 µl volume of liquid, when amounts greater than this are delivered to the eye the excess liquid will disrupt the tear film and may be rapidly blinked away. This results in the inefficient and costly loss of both liquid carrier and pharmaceutical agent.

Accordingly, it is a principal object of the present invention to provide pharmaceutical compositions which will effectively deliver water labile or poorly soluble therapeutic or diagnostic pharmaceutical compounds to aqueous physiological target sites through a wide variety of administrative routes including ingestion, injection, inhalation, topical application, sprays, mists, drops and the like. It is a further object of the present invention to provide pharmaceutical compositions for delivering water labile or poorly soluble therapeutic or diagnostic pharmaceutical compounds which exhibit improved shelf-life and stability.

It is an additional object of the present invention to provide drug delivering pharmaceutical compositions in which the therapeutic or diagnostic compounds do not prematurely leach out of the drug delivery vehicles during storage yet are released at the desired rate once administered to the target site.

It is a further object of the present invention to provide drug delivering pharmaceutical compositions intended for use in aqueous physiological systems which may be configured in multi-dose packages.

It is another object of the present invention to provide drug delivering pharmaceutical compositions capable of forming drop sizes on the order of 10 µl, that is a drop size greater than about 1 µl and less than about 20 µl, when delivered from standard dropper bottles.

It is also an object of the present invention to provide drug delivering pharmaceutical compositions having improved efficiency of delivery.

It is an additional object of the present invention to provide pharmaceutical compositions containing hydrolytically labile polymers or drugs which are intended for use in aqueous physiological milieus which are protected from premature disintegration.

It is a further additional object of the present invention to provide effective pharmaceutical compositions which are transparent, nonirritating, and do not cause vision blurring when administered to the ocular environment.

SUMMARY OF THE INVENTION

The present invention accomplishes these and other objectives by providing advantageous pharmaceutical compositions formed of drug delivery vehicles suspended in nonaqueous liquid carriers for low dose volume delivery. The pharmaceutical compositions of the present invention have improved bioavailability, provide efficient delivery of drugs in the form of low dose volumes and possess long shelf-lives with retained pharmaceutical activity and may be packaged in multi-dose configurations. Additionally, they can be formulated to stably incorporate hydrolytically labile drugs and polymers and may be administered to intended target sites through any available route of administration including small volume drop instillation methods. Unlike prior art drug delivery systems, the pharmaceutical compositions of the present invention can be delivered in dose volumes of less than 10 µl, resulting in improved drug delivery efficiency and increased bioavailability.

In accordance with the teachings of the present invention, low volume pharmaceutical compositions are preferably formed from a perfluorocarbon or fluorinated silicone liquid carrier and at least one drug delivery vehicle incorporating the desired therapeutic or diagnostic compounds. It is also contemplated as being within the scope of the present invention to form the drug delivery vehicle of polymeric particulates suspended in nonaqueous liquid carriers wherein the polymeric drug delivery vehicles incorporate a pharmaceutically effective amount of the desired therapeutic or diagnostic compounds. Preferably, the polymeric drug delivery vehicle is formed as a plurality of erodible microparticles or microcapsules which incorporate the compound of choice and are suspended in the nonaqueous liquid carrier. As those skilled in the art will appreciate, mixtures of differing erodible microparticles and microcapsules can be combined in a single carrier within the scope of the present invention to tailor the pharmaceutical composition to specific drug contents, polymer erosion rates, and drug release profiles.

Due to the nonaqueous character of the liquid carriers utilized in the pharmaceutical compositions of the present invention they are particularly suitable for suspending polymeric drug delivery vehicles prepared with hydrolytically labile polymers or pharmaceutical compounds. However, pharmaceutical compositions comprising hydrolytically stable polymeric drug delivery vehicles or pharmaceuticals are also within the scope of the present invention.

Unlike the prior art delivery systems, the pharmaceutical compositions of the present invention possess stable, long term shelf-lives without the associated loss of pharmaceutical activity of the therapeutic or diagnostic compound incorporated therein. This stability results from the fact that the therapeutic or diagnostic compound does not leach or otherwise diffuse from the microparticulates or microcapsules into the liquid carrier, but remains incorporated in the drug delivery vehicle. Similarly, where the microparticulates or microcapsules are formed of water labile polymers, they will not erode or degrade in the compositions of the present invention.

Moreover, unlike prior art aqueous and oil based delivery systems, which are limited to a minimum of about 35 μl drop sizes, the pharmaceutical compositions of the present invention form low volume doses of less than 10 μl. The pharmaceutical compositions of the present invention, preferably consisting of microparticulate or microcapsule drug delivery vehicles suspended in the liquid carriers, may be packaged and sterilized by conventional gamma irradiation techniques. Sterile fill procedures are available as an alternative to radiation sterilizing techniques. Additionally, the pharmaceutical compositions can be configured for multiple or unit dose packaging from, for example, a dropper dispenser. The unique bacteriostatic properties of the liquid carriers further facilitate the utilization of multi-dose packaging by eliminating the necessity of preservative additives commonly used in the art.

As will be discussed below, a wide variety of polymers and therapeutic and diagnostic agents can be utilized in forming the compositions of the present invention. Polymers and agents which are hydrolytically labile are particularly suitable, however, the advantageous properties of the nonaqueous compositions can be obtained with hydrolytically stable drug delivery vehicles as well.

Further objects and advantages of the nonaqueous pharmaceutical compositions of the present invention, as well as a better understanding thereof, will be afforded to those skilled in the art from a consideration of the following detailed description of preferred exemplary embodiments thereof.

DETAILED DESCRIPTION OF THE PREFERRED EMBODIMENTS

Figure 1:
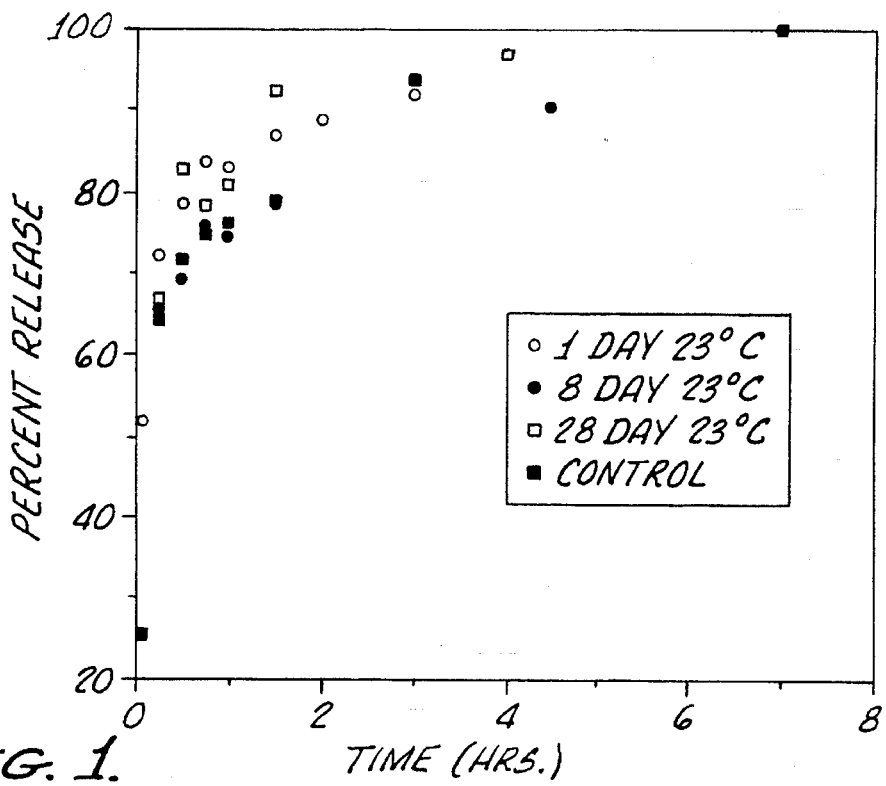
FIG. 1 is a graphical representation of the release profile of sodium fluorescein from a microparticulate suspension stored at 23° C. illustrating the principles of the present invention.

In a broad aspect, the low volume, efficient pharmaceutical compositions of the present invention comprise one or more drug delivery vehicles suspended in a perfluorocarbon or fluorinated silicone nonaqueous liquid carrier. More particularly, the pharmaceutical compositions produced in accordance with the teachings of the present invention can be formed from a perfluorocarbon or fluorinated silicone liquid carrier and, suspended in the liquid carrier, at least one drug delivery vehicle incorporating a pharmaceutically effective amount of at least one therapeutic or diagnostic compound.

Because of the bacteriostatic, nonirritating, and in fact, soothing and lubricating properties of the nonaqueous liquid carriers, the pharmaceutical compositions formed in accordance with the teachings of the present invention are particularly well suited for use in connection with the diagnosis or treatment of injuries or diseases of the eye. Further advantages associated with their ophthalmic utility are the low surface tension and high density of the nonaqueous liquid carriers, which allow for small volume drop delivery. However, those skilled in the art will appreciate that the pharmaceutical compositions of the present invention are equally well suited for use in applications to other physiological environments where the repeated administration of a drug delivery vehicle to sensitive tissue areas is desired.

Accordingly, for purposes of explanation and without limiting the scope of the present invention, where appropriate the following exemplary embodiments will be discussed in the general context of ophthalmic pharmaceutical compositions utilized for the treatment of ocular injuries and diseases. However, it should be emphasized that the pharmaceutical compositions of the present invention may be utilized through all common routes of administration such as oral, dermal, intravenous, nasal and others known in the art.

The perfluorocarbons which are preferably utilized as nonaqueous liquid carriers in the low volume, high efficiency pharmaceutical compositions of the present invention include perfluorocyclocarbons, acyclic perfluorocarbons and their derivatives. As one skilled in the art will appreciate, the perfluorocarbon derivatives are typically nitrogen and oxygen containing compounds such as amines and ethers. The nonaqueous liquid carrier compounds, however, are preferably perfluorinated, meaning that all of the hydrogens bonded to the carbons of the compound are substituted with fluorine. Thus, perfluorinated cyclic and acyclic hydrocarbons as well as the amine and ether derivatives of these compounds may be utilized in the pharmaceutical compositions of the present invention.

Exemplary perfluorocarbons which are particularly suitable for use in the pharmaceutical compositions of the present invention are blood substitutes. Perfluorocyclocarbon blood substitutes include perfluoroperhydrophenanthrene, perfluoromethylcyclohexane, perfluoro( 1,3-dimethylcyclohexane), perfluorotrimethylcyclohexane, perfluoroisopropylcyclohexane, perfluoroendotetrahydrodicyclopentadiene, perfluoro-1-methyl-4-isopropylcyclohexane, perfluoro-1-methyl-4-isopropylcyclohexane, perfluoro-n-butylcyclohexane, perfluoro(decahydronaphthalene), perfluoro (decahydro-1-methylnaphthalene), perfluoro (decahydrodimethylnaphthalene), perfluoromethyladamantane, perfluorotrimethylbicyclo(3.3.1.)nonane, and perfluorodimethylbicyclo( 3.3.1)nonane. Oxygen and nitrogen containing derivatives of perfluorocarbons which may be used as liquid carriers include perfluorotributylamine, perfluorotriisopropylamine, perfluorotetrahydrofuran and perfluoroether.

Exemplary fluorinated silicone oils for use in practicing the present invention are the polyalkylfluoroalkylmethylsiloxanes. In particular, the polytrifluoropropylmethylsiloxanes with molecular weights of between 500 and 14,000 are suitable for use in the pharmaceutical compositions of the present invention.

Preferred perfluorocarbons and fluorinated silicones have vapor pressures sufficiently low to prevent significant liquid loss caused by their evaporation from containers during storage. Fluorinated liquid carriers having ambient pressure boiling points greater than 100° C. are preferred to ensure that any evaporative losses are less than that observed for water. Additionally, exemplary preferred perfluorocarbons and fluorinated silicones have a rapid elimination half-life.

Less desirable perfluorocarbons are known to reside in fat tissues for as long as 2–3 years. Perfluoro(decahydronaphthalene) (PFD) and perfluoroperhydrophenanthrene (PPP) are preferred perfluorocarbons because of their relatively high ambient pressure boiling points, 142° C. and 215° C., respectively. Additionally, PFD and PPP have quite rapid elimination half-lives when systemically administered, the half life of PFD being about 7 days.

An additional aspect of the present invention involves suspending a polymeric drug delivery vehicle incorporating a pharmaceutically effective amount of at least one diagnostic or therapeutic compound in the perfluorocarbon or fluorinated silicone nonaqueous liquid carrier. Preferably, the polymeric drug delivery vehicle is in the form of a plurality of erodible microparticulates, each sized on the order of approximately 2 microns to 200 microns or, alternatively, a plurality of microcapsules sized on the order of approximately 20 microns to 200 microns. However, larger drug delivery vehicles such as ocular inserts are also contemplated as being within the scope of the present invention. It is also within the scope of the present invention to prepare pharmaceutical compositions comprising a mixture of particle sizes or mixtures of microcapsules and microparticulates with varying erosion rates. Such combinations can be designed to provide specific drug release profiles including high initial concentrations or so called zero order deliveries or may be utilized to provide combinations of different pharmaceutical compounds.

The solid or suspended drug delivery vehicles utilized in the pharmaceutical compositions of the present invention can be prepared through a variety of methods known to those skilled in the art. Exemplary methods for preparing microparticulates include grinding or milling mixtures of an appropriate polymer and therapeutic or diagnostic drug. Alternative methodologies include grinding or milling the polymer to form microparticulates and subsequently absorbing the drug of choice into the microparticulates so produced. Microencapsulation techniques in which emulsions of the polymer and therapeutic or diagnostic compound are coacervated to precipitate the polymer and encapsulate the compound also can be used to form microcapsule drug delivery vehicles for use in the present invention. Non-limiting examples of such formation techniques are provided below.

EXAMPLE 1

A general method for the manufacture of microparticulates involves the preparation of a stock polymer solution using 0–30% drug (preferably 0–10%) such as dipivefrin by first adding the drug to the solvent of choice such as acetone, acetonitrile, dimethylformamide, or ethyl acetate. The drug and solvent are combined and the mixture is stirred as the polymer (preferably poly(methylvinylether/maleic anhydride)) is added so polymer clumping is avoided. Mixing continues until the polymer is completely dissolved. The drug need not be completely dissolved in the solvent/polymer system, but the drug particles must be homogeneously dispersed. The mixture is then transferred to a roto-evaporator and the solvent is slowly removed. The temperature should not exceed 60° C. When all solvent is removed, the film is ground in the presence of dry ice with a small blade grinder until the appropriate sized range is achieved: 2–200 µm. For example, 5 g of poly(methylvinylether/maleic anhydride) is completely dissolved in a solution containing 100 mg dipivefrin in 95 ml of acetonitrile. This polymer stock is then added to a roto-evaporator operating at 40° C., and the acetonitrile is completely removed. The drug/polymer residue is removed from the evaporator flask and placed in a Teckmar grinder along with dry ice particles. The dry ice facilitates grinding, and the grinding takes approximately 2 minutes.

EXAMPLE 2

Alternatively, the drug/polymer stock mixture from Example 1 is roto-evaporated to dryness and the residue is first ground in a mortar and pestle and placed in a roller bottle containing glass beads with a nonaqueous diluent (preferably perfluoro(decahydronaphthalene), PFD). The suspension is ball milled for approximately three days to reach the desired 2–200 µm size range.

EXAMPLE 3

Alternatively, the drug/polymer stock mixture from Example 1 is added dropwise with agitation to an immiscible liquid (preferably mineral oil) containing 0–10% emulsifier (preferably lecithin). Microparticles are formed as polymer stock is dispersed in the immiscible phase and the polymer solvent is evaporated. Other immiscible liquids include vegetable oils, silicone oils, and perfluorocarbons. The ratio of polymer stock solution to immiscible phase should not exceed 1:3 v/v. The final particle size distribution of the particles is dependent on the degree of agitation and the viscosity of the immiscible material. Generally, a pneumatic mixer rotating at approximately 300 rpm gives the desired particle size range. Once all of the polymer solvent is evaporated from the particles, the particles are cleaned several times with a solvent, typically hexane.

Exemplary polymers suitable for incorporating therapeutic or diagnostic compounds in accordance with the teachings of the present invention are those polymers which are compatible with both the target tissue and with the therapeutic or diagnostic compound of choice. Included within this class of polymers are both hydrolytically stable and hydrolytically labile polymers. Those skilled in the art, however, will appreciate that polymeric drug delivery vehicles prepared from polymers which are hydrolytically labile are particularly well suited for use with the perfluorocarbons or fluorinated silicone carriers of the present invention as they are stable in solution yet will erode in the aqueous environment of the target site and thereby eliminate themselves from the site as their pharmaceutical compounds are delivered.

Exemplary hydrolytically stable polymers which are suitable for use in the polymeric drug delivery vehicles include acrylate, ethylene vinylacetate, silicones, polyurethanes, and polysulfones. Exemplary polymers which are labile in an aqueous environment include poly(methylvinylether/maleic anhydride), polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine.

A preferred exemplary aqueous labile polymer is Gantrez AN, a Poly(methylvinylether/maleic anhydride) available from GAF. Upon contact with an aqueous medium the anhydride functionalities of this polymer readily hydrolyze to form the free acid. This initial hydrolysis leads to the formation of a hydrogel with soft bioadhesive properties. As hydrolysis proceeds, the poly(methylvinylether/maleic anhydride) dissolves, and during the dissolution process the incorporated drug is continuously released. However, in accordance with the teachings of the present invention, pharmaceutical compositions prepared from Gantrez AN microparticulate or microcapsule drug delivery vehicles suspended in a perfluorocarbon carrier do not prematurely erode and release the incorporated drug. Similarly, they do not release the incorporated drug during storage and provide a long-shelf life, yet they are very effective when delivered to the aqueous target environment.

An alternative hydrolytically labile polymer drug delivery system can be formed from those compounds which have ionic side chains capable of complexing with a drug of opposite ionic charge. Microparticulates formed of these polymers erode in the aqueous physiological environment and dissociate the drug which is ionically bound to the polymer thereby delivering the drug to the target site. Pharmaceutical compositions prepared from these ionic polymers suspended in a nonaqueous carrier such as perfluorocarbon do not prematurely release the ionically bound drug and therefore can be prepared in stable, multi-dose forms.

Any pharmaceutical compound which is suitable for therapeutic or diagnostic purposes and is compatible with a suitable polymer may be incorporated in the drug delivery vehicle of the present invention. Exemplary pharmaceutical compounds included protein growth factors, oligopeptides, antibacterial, antihistaminic, anti-inflammatory, miotic, anticholinergic, mydriatic, antiglaucoma, antiparasitic, antiviral, carbonic anhydrase inhibitor, antifungal, anesthetic, diagnostic and immunosuppressive agents. Preferred pharmaceutical compounds for use in ocular situations include epithelial growth factor, levo-bunolol hydrochloride, UK-14304-18, pilocarpine, dipivefrin (DPE), sodium fluorescein, tetracycline, chlortetracycline, bacitracin, neomycin, polymyxin, gramicidin, tobramycin, ciprofloxacin, norfloxacin, penicillin, erythromycin, cefazolin, ceftazidime, imipenem, idoxuridine, hydrocortisones, dexamethasone, dexamethasone 21 phosphate, fluocinolone, medrysone, prednisolone acetate, fluormetholone, betamethasone, phenylephrine, eserine salicylate, carbachol, echothiophate iodide, demecarium bromide, cyclopentolate, homatropine, scopolamine, epinephrine, ibuprofen, aceclidine, teretinoin, and pirenoxine.

The amount of therapeutic or diagnostic compound incorporated in the polymer is dependent upon the compound of choice, the required dose, and the form of the drug delivery vehicle. The effective amount normally ranges from a few percent up to 60% by weight of the polymer with microparticles generally having smaller amounts than microcapsules.

Contributing to the economies of the present invention, the pharmaceutical compositions may be prepared by methods known in the art for formulating drug delivery vehicles suspended in a liquid carrier. The amount of drug delivery vehicle suspended in the carrier liquids of the present invention depends upon the dose configuration and the desired dose volume. For single dose units packaged in dropper style delivery systems the volume ratio of carrier liquid to microparticulate ranges from about 99.0 to about 5.0. Volume ratios for packaging configurations designed for multiple uses typically range from about 99.9 to about 3.0 liquid carrier to microparticulate. Preferably, the weight to volume ratio of suspended drug delivery vehicle to nonaqueous carrier liquid will range from approximately 0 to 10%. However, those skilled in the art will appreciate that these ratios are appropriately adjusted to adapt to the intended applications, target sites and pharmaceutical compounds utilized in accordance with the teachings of the present invention.

Preferably, the low volume, high efficiency pharmaceutical compositions of the present invention are finally packaged in sterile condition. This may be achieved through formulation procedures utilizing sterile fill methods and heat or gamma irradiation techniques to obtain a sterile product. One exemplary approach to producing a sterile pharmaceutical composition may be utilized when the desired microparticulate size is obtained with wet milling procedures utilizing a nonaqueous liquid carrier. Such a procedure includes sterilizing the drug/polymer stock powder mixture using a suitable sterilizing method such as heat or gamma irradiation, and sterile filtering the selected perfluorocarbon or fluorinated silicone. The sterile drug/polymer stock powder is then aseptically combined with the sterile nonaqueous liquid carrier and the mixture is wet milled until the desired particle size is reached. The final product is then aseptically filled into the desired package configuration.

Another procedure for obtaining sterile pharmaceutical compositions of the present invention includes dry milling drug/polymer stock to the desired particle size followed by sterilizing the resulting microparticulates. The sterile dry powders are then aseptically added to a previously sterile filtered perfluorocarbon or fluorinated silicone.

The following additional non-limiting examples are illustrative of methods used for formulating the pharmaceutical compositions of the present invention.

EXAMPLE 4

To produce a microparticulate drug delivery vehicle suspended in a nonaqueous carrier the dry powder microparticulate drug delivery vehicles produced from the grinding procedure of the Example 1 are simply added to perfluoro-(decahydronaphthalene) (PFD) in a preferred ratio of from 0 to 10% w/v. Sonic agitation may be utilized to assist in the even distribution of the microparticulates.

EXAMPLE 5

Alternatively, the microparticulate drug delivery vehicle produced utilizing the ball milling procedure of Example 2 can be utilized as follows. As a preliminary step the drug containing microparticulates are separated from the glass beads of the ball mill. Where the nonaqueous diluent in the ball milling procedure is the preferred nonaqueous carrier liquid, such as PFD the separated microparticulate suspension is simply diluted to the desired concentration, preferably ranging from approximately 0 to 10% w/v utilizing addition of PFD. As those skilled in the art will appreciate, where alternative grinding solvents are utilized additional separation may be necessary as is known in the art prior to preparing the suspension.

EXAMPLE 6

Alternatively, microparticulate drug delivery vehicles produced through the emulsion technique of Example 3 may be utilized to form the pharmaceutical compositions of the present invention as follows. Once the microparticulates produced through solvent evaporation are washed with the appropriate solvent, preferably hexane, the microparticulates are dried in a vacuum oven until all residual hexane is removed. The dried particles are simply added to PFD or other nonaqueous carrier liquids in the desired proportions, preferably ranging from approximately 0 to 10% w/v.

It is additionally contemplated as being within the scope of the present invention to incorporate surfactants and/or suspending agents in the pharmaceutical compositions. The presence of surfactants or suspending agents assists in the formation of stable uniform suspension of microparticulates in perfluorocarbon or fluorinated silicones. Stable suspensions in turn contribute to the ability to deliver a consistent, low volume dose regimen over the life of the pharmaceutical composition. Suitable exemplary pharmaceutically acceptable surfactants include non-ionic ethoxylated alcohols and sorbitans. Included in the group of acceptable surfactants are the Pluronics, Tweens, Polyethylene glycols, Spans, lecithin and oleic acid which act to neutralize residual static charges on the particles and to prevent aggregation. Suspending agents include simple sugars, salts, synthetic polymers, polysaccharides and celluloses, etc., which act to prevent particle settling through steric collisions. Which suspending agents and surfactants are preferred will be dependent upon the particular polymer and perfluorocarbon or fluorinated silicone utilized in a specific pharmaceutical composition and can be determined utilizing routine stability testing procedures.

As will be appreciated by those skilled in the art, the exemplary perfluorocarbon and fluorinated silicone liquids utilized in the pharmaceutical compositions of the present invention provide unique chemical and physical properties which make them particularly well suited for use as nonaqueous liquid carriers for polymeric drug delivery vehicles. More particularly, they are chemically and physically stable. Thus, drug delivery vehicles prepared from virtually any suitable polymer and drug combination may be suspended in the perfluorocarbon or fluorinated silicone liquid carriers for extended periods of time without unwanted interactions between the carrier and the polymer or drug.

In addition to these enhanced liquid storage properties, the pharmaceutical compositions produced in accordance with the techniques of the present invention also have unexpectedly improved shelf-lives when compared with pharmaceutical compositions stored in a sterile, dry state. It is believed that the hydrophobic nature of the compositions precludes small amounts of oxygen and moisture from gaining access to the drug delivery vehicles, and thus they remain viable and pharmaceutically active for an extended period of time.

In contrast, prior art drug delivery vehicles formed from hydrolytically labile polymers can not be suspended for long term storage in aqueous carriers. Normally, these vehicles are packaged and stored in the dry state in order to achieve reasonable shelf-lives. Users of drug delivery vehicles which are stored without the benefit of being suspended in a carrier liquid are inconvenienced by the necessity of having to suspend the vehicles in a sterile aqueous carrier just prior to delivery to the target site.

The perfluorocarbon or fluorinated silicone suspension vehicles utilized in the present invention provide a unique and advantageous alternative to storing labile microparticles or microcapsules in the dry state. The pharmaceutical compositions prepared in accordance with the present invention are "user friendly" in that they are available in ready to use pre-mixed preparations.

As noted above, an equally beneficial property of the pharmaceutical compositions of the present invention is their ability to remain stable for a long period of time without leaching or loss of the pharmaceutical compound from the polymeric drug delivery vehicle into the liquid carrier. The pharmaceutical compounds are effectively locked in to the delivery vehicle until the formulation is administered to the desired physiological site. There, the nonaqueous carrier solution is replaced by the aqueous physiological fluid at the target site which initiates release of the incorporated pharmaceutical compound.

This is specially important when the polymeric drug delivery vehicle utilized to form the pharmaceutical composition is a hydrolytically labile polymer. As those skilled in the art will appreciate, hydrolytically labile polymers are characterized by their ability to physically or chemically erode in an aqueous environment. This erosion occurs over a period of time by any of a number of different processes such as enzymatic degradation, hydrolysis, or solubilization in response to contact with an aqueous physiological environment. Thus, when a drug delivery vehicle which is formed from a hydrolytically labile polymer and an incorporated pharmaceutical compound is placed in the ocular environment, it erodes in a manner that results in the release or delivery of the drug to the eye.

The following examples are illustrative of the enhanced shelf life and prolonged stability of exemplary pharmaceutical compositions produced in accordance with the teachings of the present invention.

EXAMPLE 7

Figure 2:
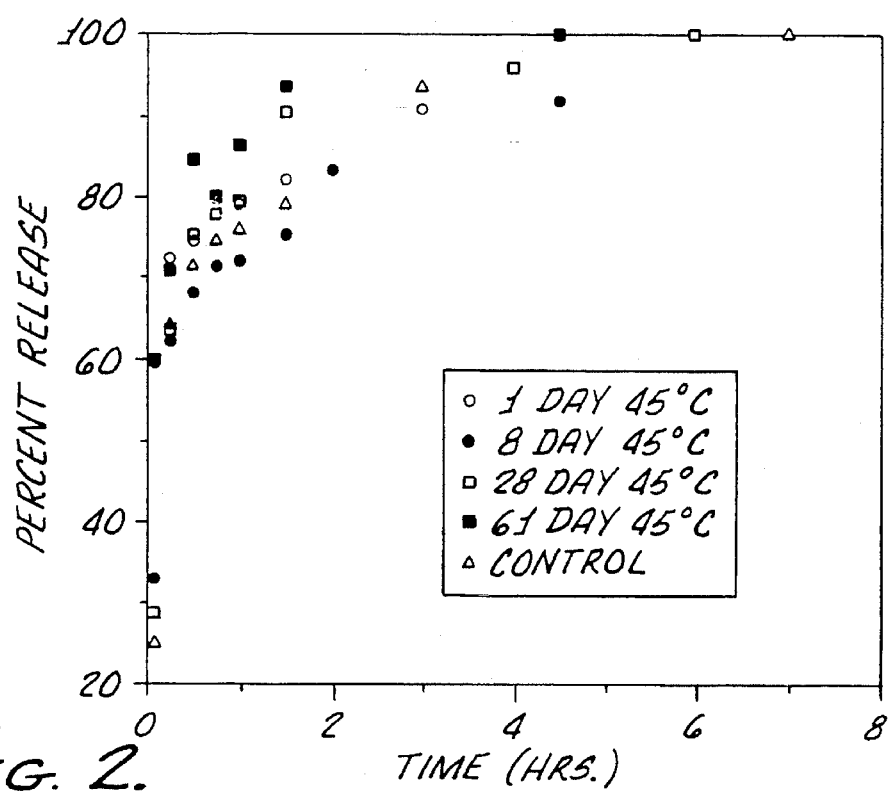
FIG. 2 is a graphical representation of the release profile of sodium fluorescein from a microparticulate suspension stored at 45° C. illustrating the principles of the present invention.

In order to determine the temperature stability and release profile of the nonaqueous drug delivery vehicle suspensions of the present invention microparticulates containing 5% sodium fluorescein were prepared utilizing poly(methylvinylether/maleic anhydride) as the polymer matrix utilizing the manufacturing technique of Example 1 and were suspended in PFD as a 2% w/v suspension utilizing the technique of Example 4. This nonaqueous drug delivery vehicle suspension was divided in half and equal portions were stored at 23° C. and at 45° C. for thirty days. Samples were taken of each portion during the thirty day test period and fluorescein release profiles were obtained as is known in the art. More specifically, the dissolution tests were performed as follows. 500 ml of 7.4 pH phosphate buffer (0.05M) was added to the kettles in the standard USP dissolution apparatus set at 37° C. 10 ml of the 2% w/v suspension was slowly added to the dissolution medium and the propeller speed was set to 50 rpm. Over a seven hour time period, samples were taken from the dissolution medium and immediately centrifuged. The supernatant containing the released fluorescein was assayed for fluorescein content by UV spectrophotometry. Release profiles for the 23° C. and 45° C. samples are given in FIGS. 1 and 2. The control was freshly prepared microparticulates.

EXAMPLE 8

Figure 3:
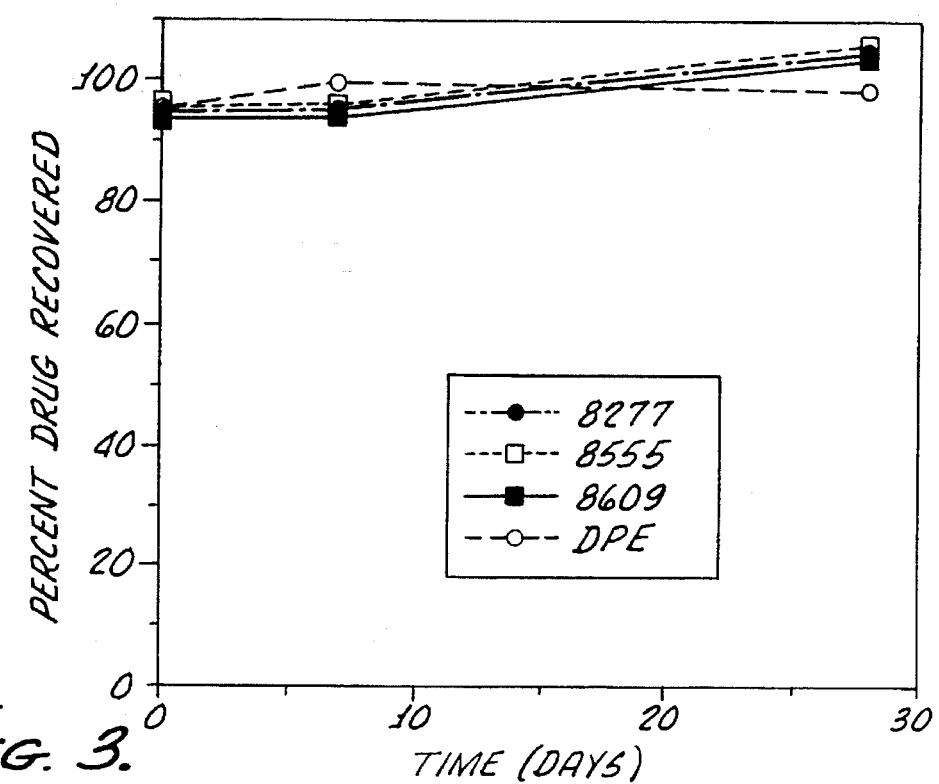
FIG. 3 is a graphical representation of the temperature stability profile of a water labile drug containing microparticulate suspension stored at 37° C. illustrating the principles of the present invention.
Figure 4:
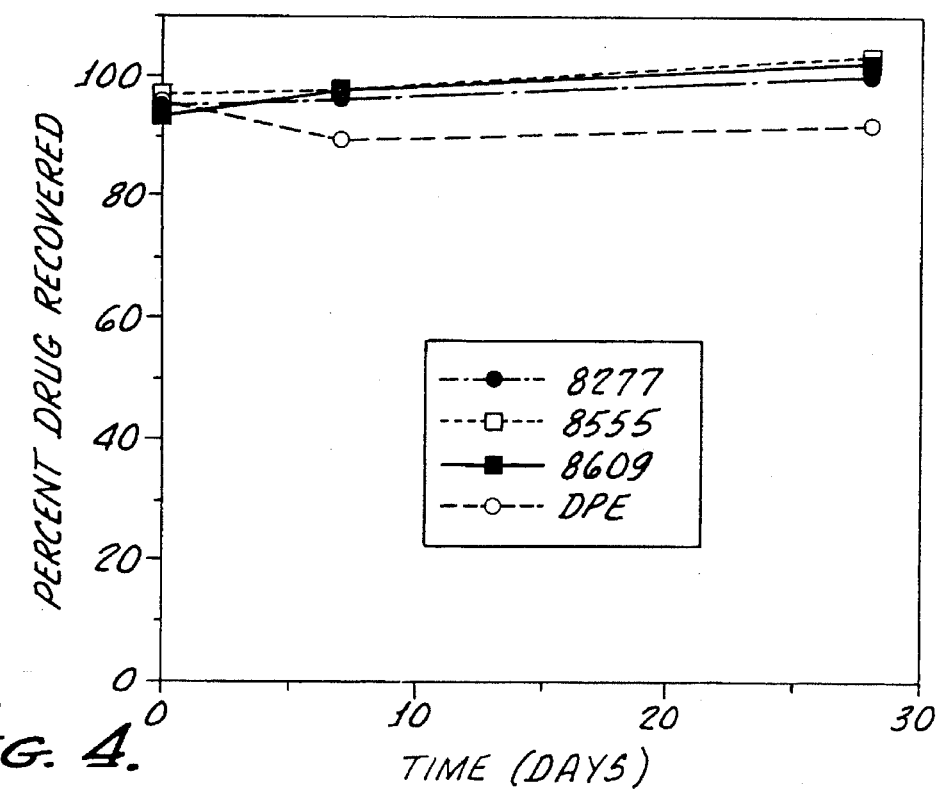
FIG. 4 is a graphical representation of the temperature stability profile of a water labile drug containing microparticulate suspension stored at 23° C. illustrating the principles of the present invention.

An additional set of experiments was performed to determine if a water labile drug was stable in the suspended drug delivery vehicle when stored in the preferred nonaqueous carrier liquid, PFD. Microparticulates containing 2% dipivefrin (DPE) were prepared from three different lots of poly(methylvinylether/maleic anhydride) obtained from GAF, Inc. (Lot #8277, 8555, and 8609) utilizing the microparticulate production technique of Example 1. The ground microparticulates were added to PFD to form a 5% w/v suspension. As with Example 7, portions of this suspension were stored at different temperatures for thirty days. One portion was stored at 23° C. (essentially ambient temperature) and a second portion at 37° C. At various intervals during this thirty day period samples were taken from each portion and the microparticulates were extracted from the PFD phase using acetonitrile. The content of undegraded DPE and known degradants in the acetonitrile phase were then assayed using HPLC. Results of these experiments are given in FIGS. 3 and 4. The control, labeled "DPE", was 0.1% dipivefrin in perfluorodecalin.

As those skilled in the art will appreciate, the foregoing examples illustrate the outstanding long-term storage stability of the pharmaceutical compositions of the present invention as well as the consistent drug release rates following storage at varying temperatures.

Advantageously, the nonaqueous liquid carriers utilized to form the low volume pharmaceutical compositions of the present invention are soothing, non-irritating and non-toxic. Thus, their use in physiological applications, and in particular the ocular environment, is particularly suitable. The experiment described in Example 9 illustrates and confirms this non-toxicity of an exemplary pharmaceutical composition of the present invention.

EXAMPLE 9

In order to evaluate the in vivo toxicity characteristics of the pharmaceutical composition of the present invention, an in vivo toxicity probe study was performed in rabbit eyes. Microparticles of 5 w/w % DPE in Gantrez AN169 (a polyvinylether maleic anhydride) were prepared and suspended in perfluorodecalin. Two suspensions were studied, the first contained 2 w/v % microparticulate in perfluorodecalin and the second contained 5 w/v % microparticulate in perfluorodecalin. Because Gantrez AN169 is water labile, no comparable study in an aqueous suspension was possible. Each suspension was administered to rabbit eyes and no adverse effects were observed.

As an added benefit, the pharmaceutical compositions of the present invention can be packaged for multi or single dose use. The availability of the option for multi-dose packaging is a significant advantage over single dose or unit dose packaging which is required for many pharmaceutical compositions. Single dose packing is more costly and many users prefer the convenience of, for example, large volume eye dropper delivery designs for multi-dose applications.

Additionally, unlike aqueous based pharmaceutical compositions which will support the growth of bacteria if preservatives are not used, the pharmaceutical compositions of the present invention have bacteriostatic properties. These bacteriostatic properties make it possible to provide pharmaceutical compositions without preservative additives and the possible side effects thereof. This is particularly advantageous for users of ophthalmic preparations who have a sensitivity to preservatives. Additionally, when the pharmaceutical compositions of the present invention are packaged in multi-dose configurations they can be sterilized once and then repeatedly opened and reused without fear of the subsequent growth of harmful organisms in the liquid carrier.

Other beneficial characteristics of the pharmaceutical compositions of the present invention derive from their ability to operate in the ocular environment with minimal vision disruption. The nonaqueous carriers utilized in the pharmaceutical compositions have refractive indices which are very close to that of water. What is more, they are immiscible with both the lipid layer and the aqueous layer of the ocular tear film. This immiscibility reduces disruptive interaction with the tear film layers. Additionally, the advantageously small drop size and nearly identical refractive indices of the nonaqueous compositions and the aqueous layer of the tear film substantially eliminates the vision perturbation commonly associated with the use of current nonaqueous pharmaceutical carriers such as mineral oils.

As an added functional benefit, the preferred perfluorocarbon carriers have specific gravities in excess of 1.2. As a result, when utilized in conjunction with suspended microparticles or microcapsules delivered to the cul-de-sac of the eye, this relatively high specific gravity, coupled with the carriers' immiscibility with the aqueous layer of the tear film, causes the carrier to separate rapidly from the particulate vehicle and to drain from the eye through the lacrimal duct while leaving the slow release carrier in the intended aqueous environment.

In accordance with the teachings of the present invention, the pharmaceutical composition so produced may be utilized to deliver therapeutic or diagnostic agents to physiological target sites including the eye or other similar environments through any currently available administration route.

An exemplary method for delivering therapeutic or diagnostic compounds comprises the steps of providing a pharmaceutical composition of a perfluorocarbon liquid carrier and at least one therapeutic or diagnostic drug containing delivery vehicle suspended therein and administering a low volume yet effective dosage of the pharmaceutical composition to the target site. The administration route can be through injection, oral ingestion, nasal inhalation, topical application, eye drops or any other currently available administration route due to the broad applicability of the compositions of the present invention.

The beneficial delivery characteristics of the low volume, high efficiency pharmaceutical compositions of the present invention are produced by the physical properties of the fluorinated liquid carriers. More specifically, the high densities (typically greater than 1.2) and low surface tensions of perfluorocarbons and fluorinated silicones allow users to deliver dose volumes as low as 8 μl from standard dropper delivery systems. The human ocular tear film is capable of accommodating volumes of only about 7 μl. Thus, the ability to deliver small volumes to the eye results in little or no costly loss of drugs which are largely blinked away when the prior art 35 μl–50 μl volume oil and water liquid carrier delivery compositions are utilized to deliver pharmaceutical agents to the eye.

Accordingly, the present invention provides pharmaceutical compositions in the form of highly efficient, low dose volume, drop instillable mixtures of a nonaqueous physiologically acceptable perfluorocarbon liquid carrier and at least one drug polymeric delivery vehicle incorporating a pharmaceutically effective amount of a therapeutic or diagnostic compound. The low dose volumes are preferably less than 10 μl. Preferably, the low dose volume, drop instillable mixtures are produced in the form of liquid suspensions of at least one polymeric drug delivery vehicle suspended in perfluorocarbon liquid carrier. Moreover, the preferred dose configuration of the pharmaceutical compositions of the present invention include a plurality of polymeric drug delivery vehicles in the form of microparticulates suspended in a perfluorocarbon liquid carrier.

Table I illustrates the dramatic distinction between the physical characteristic of water and that of two perfluorocarbons, PFD and PPP. The high density and remarkable low surface tension allows very small drop volumes to be formed with standard liquid droppers. By contrast, water is limited to forming drops in the range of 35 μl–50 μl. Thus, the compositions of the present invention can be utilized to form advantageously small eye drops with standard droppers.

TABLE I

|  | Water | PFD | PPP |
|---|---|---|---|
| Molecular weight | 18 | 462 | 624 |
| Boiling point (°C.) | 100 | 142 | 215 |
| Refractive index | 1.333 | 1.31 | 1.33 |
| Density @ 25° C. (gms/mL) | 1.000 | 1.929 | 2.016 |
| Kin. viscosity @ 25° C. (cSt) | 1.00 | 2.9 | 8.0 |
| Heat of vaporization (g-cal/gm) | 539.0 | 16.1 | 15.9 |
| Specific heat @ 25° C. (g-cal/gm) | 1.00 | 0.22 | 0.27 |
| Surface tension @ 25° C. (dynes/cm) | 72.0 | 19.3 | 21.6 |

Furthermore, as illustrated in Example 10, the bioavailability of pharmaceutical compounds utilized in the low volume, high efficiency pharmaceutical compositions of the present invention is substantially higher than pharmaceutical compounds delivered in larger drop aqueous systems.

EXAMPLE 10

A comparison of the pharmokinetic and pharmacologic characteristics of pilocarpine suspended in the perfluorocarbon versus pilocarpine in an aqueous solution was conducted on rabbits. This study involved delivering an 8 µl dose of pilocarpine suspended in the perfluorocarbon to rabbits' eyes and a corresponding 35 µl dose of the aqueous pilocarpine solution. The amount of pilocarpine actually retained by the eye following delivery was quantitatively determined for both the perfluorocarbon based delivery and for the aqueous based delivery. It was observed that by delivering pilocarpine in the low volume perfluorocarbon suspension a 2.4 times higher concentration of pilocarpine would remain in the eye as compared to the aqueous based 35 µl dose of pilocarpine when the concentration is corrected for the total dose used. The study also showed that the pharmacological activity of pilocarpine delivered in the perfluorocarbon suspension lasted 1 to 2 hours longer than the pharmacologic activity of pilocarpine delivered in the aqueous carrier. The results of this study illustrate the significantly greater efficiency and bioavailability associated with pharmaceutical compounds delivered using the perfluorocarbon liquid carriers of the present invention.

Having thus described exemplary embodiments of the present invention, it should be noted by those skilled in the art that the disclosures herein are exemplary only and that alternatives, adaptations and modifications may be made within the scope of the present invention. Accordingly, the present invention is not limited to the specific embodiments illustrated herein.

What is claimed is:

1. A low delivery volume nonaqueous pharmaceutical composition displaying the property of enhanced drug bioavailability at a physiological target site and reduced side effects, said composition comprising:
a drop instillable mixture of a nonaqueous, physiologically acceptable perfluorocarbon liquid carrier and a pharmaceutically effective amount of a therapeutic or diagnostic compound incorporated in a particulate polymer drug delivery vehicle, said mixture having a delivery volume on the order of 10 µl.

2. The low delivery volume pharmaceutical composition of claim 1 wherein said delivery volume is greater than about 1 µl and less than about 10 µl.

3. The low delivery volume pharmaceutical composition of claim 1 wherein said delivery volume is about 4 µl to about 8 µl.

4. The low delivery volume pharmaceutical composition of claim 1 wherein said mixture includes a surfactant.

5. The low delivery volume pharmaceutical composition of claim 1 wherein said nonaqueous physiologically acceptable perfluorocarbon liquid carrier is selected from the group consisting of perfluoro (decahydronaphthalene), perfluoro-(decahydro-1-methylnaphthalene), perfluoro (decahydrodimethylnaphthalene), perfluoroperhydrophenanthrene, perfluoromethylcyclohexane, perfluoro(1,3-dimethylcyclohexane), perfluorotrimethylcyclohexane, perfluoroisopropylcyclohexane, perfluoro-1-methyl-4-isopropylcyclohexane, perfluoro-n-butylcyclohexane, perfluoroendotetrahydrodicyclopentadiene, perfluoromethyladamantane, perfluorodimethylbicyclo (3.3.1.) nonane, and perfluorotrimethylbicyclo(3.31.) nonane.

6. The low delivery volume pharmaceutical composition of claim 1 wherein said nonaqueous physiologically acceptable perfluorocarbon liquid carrier is selected from the group consisting of perfluorotributylamine and perfluorotriisopropylamine.

7. The low delivery volume pharmaceutical composition of claim 1 wherein said nonaqueous physiologically acceptable perfluorocarbon liquid carrier is selected from the group consisting of perfluorotetrahydrofuran and perfluoroether.

8. The low delivery volume pharmaceutical composition of claim 1 wherein said therapeutic or diagnostic compound is selected from the group consisting of oligopeptides, antibacterials, antihistaminics, anti-inflammatories, miotics, mydriatics, antiglaucomals, antivirals, carbonic anhydrase inhibitors, antifungals, anesthetics, diagnostics, immunosupporessive agents, and mixtures thereof.

9. The low delivery volume pharmaceutical composition of claim 1 wherein said polymeric drug delivery vehicle is a hydrolytically labile polymer selected from the group consisting of poly(methylvinylether/maleic anhydride), polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine.

10. The low delivery volume pharmaceutical composition of claim 1 wherein said polymeric drug delivery vehicle comprises a plurality of microparticulates, each of said microparticulates being formed of a polymeric matrix incorporating said therapeutic or diagnostic compound.

11. The low delivery volume pharmaceutical composition of claim 10 wherein each of said microparticulates is sized from approximately 2 microns to 200 microns.

12. The low delivery volume pharmaceutical composition of claim 10 wherein said microparticulates are microcapsules, each of said microcapsules being formed of an erodible polymer encapsulating said therapeutic or diagnostic compound.

13. The low delivery volume pharmaceutical composition of claim 10 wherein said polymeric matrix is a hydrolytically labile polymer selected from the group consisting of poly(methylvinylether/maleic anhydride), polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine.

14. The low delivery volume pharmaceutical composition of claim 1 wherein said therapeutic or diagnostic compound is selected from the group consisting of protein growth factors, anticholinergics and antiparasitics.

15. An enhanced drug bioavailability nonaqueous pharmaceutical composition exhibiting a drop delivery volume on the order of 10 μl, said composition comprising a mixture of a nonaqueous physiologically acceptable perfluorocarbon liquid carrier and a therapeutic or diagnostic compound incorporated in a particulate polymeric drug delivery vehicle.

16. The enhanced drug bioavailability pharmaceutical composition of claim 15 wherein said mixture is a suspension in said nonaqueous physiologically acceptable perfluorocarbon liquid carrier of said therapeutic or diagnostic compound incorporated in said polymeric dug delivery vehicle.

17. The enhanced drug bioavailability pharmaceutical composition of claim 16 wherein said suspension includes a surfactant.

18. The enhanced drug bioavailability pharmaceutical composition of claim 15 wherein said nonaqueous physiologically acceptable perfluorocarbon liquid carrier is selected from the group consisting of perfluoro (decahydronaphthalene), perfluoro (decahydro- 1-methylnaphthalene), perfluoro (decahydrodimethylnaphthalene), perfluoroperhydrophenanthrene, perfluoromethylcyclohexane, perfluoro(1,3-dimethylcyclohexane), perfluorotrimethylcyclohexane, perfluoroisopropylcyclohexane, perfluoro-1-methyl-4-isopropylcyclohexane, perfluoro-n-butylcyclohexane, perfluoroendotetrahydrodicyclopentadiene, perfluoromethyladamantane, perfluorodimethylbicyclo(3.3.1.) nonane, and perfluorotrimethylbicyclo(3.3.1) nonane.

19. The enhanced drug bioavailability pharmaceutical composition of claim 15 wherein said nonaqueous physiologically acceptable perfluorocarbon liquid carrier is selected from the group consisting of perfluorotributylamine and perfluorotriisopropylamine.

20. The enhanced drug bioavailability pharmaceutical composition of claim 15 wherein said nonaqueous physiologically acceptable perfluorocarbon liquid carrier is selected from the group consisting of perfluorotetrahydrofuran and perfluoroether.

21. The enhanced drug bioavailability pharmaceutical composition of claim 15 wherein said therapeutic or diagnostic compound is selected from the group consisting of oligopeptides, antibacterials, antihistaminics, anti-inflammatories, miotics, mydriatics, antiglaucomals, antivirals, carbonic anhydrase inhibitors, antifungals, anesthetics, diagnostics, immunosupporessive agents, and mixtures thereof.

22. The enhanced drug bioavailability pharmaceutical composition of claim 15 wherein said polymeric drug delivery vehicle comprises a plurality of microparticulates, each of said microparticulates being formed of a polymeric matrix incorporating said at least one therapeutic or diagnostic compound.

23. The enhanced drug bioavailability pharmaceutical composition of claim 15 wherein said polymeric drug delivery vehicle is a hydrolytically labile polymer selected from the group consisting of poly(methylvinylether/maleic anhydride), polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine.

24. The enhanced drug bioavailability pharmaceutical composition of claim 15 wherein said therapeutic or diagnostic compound is selected from the group consisting of protein growth factors, anticholinergics and antiparasitics.

* * * * *